United States Patent [19]
Thomas et al.

[11] Patent Number: 6,086,826
[45] Date of Patent: Jul. 11, 2000

[54] PRESSURE SENSING REACTION VESSEL FOR MICROWAVE ASSISTED CHEMISTRY

[75] Inventors: James Edward Thomas, Harrisburg; Wyatt Price Hargett, Jr., Matthews; Edward Earl King, Charlotte, all of N.C.

[73] Assignee: CEM Corporation, Matthews, N.C.

[21] Appl. No.: 08/929,589

[22] Filed: Sep. 15, 1997

[51] Int. Cl.[7] .............................. B01J 19/12; G01N 1/44
[52] U.S. Cl. ...................... 422/102; 422/82.13; 422/112; 422/117; 422/119; 436/148; 436/155; 219/678
[58] Field of Search .................... 422/102, 22, 82.13, 422/105, 112, 117, 119; 436/148, 155; 219/756, 678, 679; 73/726, 727

[56] References Cited

U.S. PATENT DOCUMENTS

| | | |
|---|---|---|
| Re. 34,373 | 9/1993 | Collins et al. . |
| 4,566,312 | 1/1986 | Collins et al. . |
| 4,681,996 | 7/1987 | Collins et al. . |
| 4,882,128 | 11/1989 | Hukvari et al. ............ 422/119 |
| 4,882,286 | 11/1989 | Neas et al. . |
| 4,932,266 | 6/1990 | Bauer et al. ................ 73/727 |
| 5,066,843 | 11/1991 | Revesz . |
| 5,206,479 | 4/1993 | Zakaria et al. . |
| 5,264,185 | 11/1993 | Floyd . |
| 5,369,034 | 11/1994 | Hargett et al. . |
| 5,520,886 | 5/1996 | Bennett et al. . |
| 5,637,803 | 6/1997 | Schalk et al. . |

FOREIGN PATENT DOCUMENTS

| | | |
|---|---|---|
| 0416759 A1 | 3/1991 | European Pat. Off. . |
| 3919601 A1 | 12/1989 | Germany . |
| 4300957 A1 | 7/1994 | Germany . |

OTHER PUBLICATIONS

"Comparison of Microwave Assisted and Convention Leaching Using EPA Method 3050B," ElkeM. L. Lorentzen and H. M. "Skip" Kingston, Analytical Chemistry, vol. 68, No. 24, pp. 4316–4320, 1996.

*Primary Examiner*—Long V. Le
*Attorney, Agent, or Firm*—Philip Summa, P.A.

[57] ABSTRACT

A microwave vessel system for external and noninvasive pressure monitoring and control is disclosed. The system comprises a reaction vessel formed of a material that is transparent to microwave radiation, with the reaction vessel including a portion that is movable under pressure generated by a chemical reaction inside the vessel while maintaining the reaction sealed inside the vessel. A sensor is adjacent to the movable portion of the vessel for detecting the motion of the movable portion as the portion responds to pressure generated inside the vessel. The system includes a structure for maintaining the sensor against the movable portion while microwaves are applied to the vessel so that the movement of the movable portion under pressure is detected by the sensor.

20 Claims, 4 Drawing Sheets

PRESSURE SENSING REACTION VESSEL FOR MICROWAVE ASSISTED CHEMISTRY

FIELD OF THE INVENTION

The present invention relates to microwave assisted chemistry techniques and apparatus, and in particular, relates to the external and noninvasive measurement of pressure generated in closed vessels by chemical reactions that are microwave assisted.

BACKGROUND OF THE INVENTION

The term "microwave assisted chemistry" refers to the use of electromagnetic radiation within the microwave frequencies to provide the energy required to initiate, drive, or accelerate certain chemical reactions. As chemists have long been aware, the application of heat energy is one of the most significant factors in increasing the rate of a wide variety of chemical reactions. Thus, generally familiar devices such as the Bunsen burner, other types of gas burners, hot plates, and other similar devices have historically been used to initiate or accelerate various chemical reactions.

As a relatively crude comparison, microwave assisted chemistry techniques are used to heat chemical reagents in the same way that a consumer microwave oven cooks food. There are significant differences, however, between the ordinary consumer use of microwave energy with food and its laboratory use with chemical reagents. Thus, the devices and techniques required for microwave assisted chemistry are generally much more sophisticated than are the consumer-oriented devices and techniques.

In one comparison, however, a laboratory microwave device and a consumer microwave offer the same advantage: in many circumstances they both greatly increase the rate at which materials can be heated as compared to the rates that they could be heated by ordinary conduction or convection heating. Thus, microwave assisted chemistry has been particularly valuable in driving or accelerating reactions that tend to be time-consuming under more conventional heating techniques. Particular examples include moisture analysis, in which samples must effectively be heated to dryness; digestion, a process in which a chemical composition is broken down into its elements for further analysis, with the breakdown generally being accomplished by heating the composition in one or more mineral acids; and the Kjeldahl techniques for nitrogen determination. Using conventional heating techniques, moisture analysis, Kjeldahl, or digestion reactions can be very lengthy, extending for hours in some cases. When the reactions are microwave assisted, however, they can be completed in a much shorter period of time. It will be understood that this time savings has a particularly significant advantage in any situation in which large number of samples must be tested on an almost continuous basis. Thus, although microwave assisted chemistry is relatively new compared to some other techniques, it has become well established and accepted in a number of analytical applications.

As well understood by those familiar with the electromagnetic spectrum, the term "microwave" is often used generically to refer to radiation with wavelengths of between about 1000 and 500,000 microns ($\mu$), and corresponding frequencies of between about $1 \times 10^9$ and $5 \times 10^{11}$ Hertz (Hz). These are arbitrary boundaries, however, and other sources refer to microwaves as having frequencies of between about $10^8$ Hz and $10^{12}$ Hz and wavelengths of between about 300 centimeters (cm) and 0.3 millimeters (mm). For commercial and consumer purposes in the United States, the available microwave frequencies are regulated by the Federal Communications Commission and are generally limited to certain frequencies such as 2450 megahertz (MHz). Because of the relatively long wavelength of microwave radiation, microwave assisted chemistry techniques are often carried out in closed vessels which are in turn placed inside a device that bears a superficial relation to a consumer microwave oven, but that is much more sophisticated in its source, waveguide, cavity, and control elements.

In turn, because the reactions are often carried out inside closed vessels, and because the reactions often generate gas, the reactions tend to generate and build up significant pressure in the reaction vessels. Accordingly, vessels have been developed to withstand most expected pressures, and also to include various pressure relief devices to prevent the vessels from exploding under the significant pressures being generated. An exemplary vessel and pressure release system is set forth, for example in U.S. Pat. No. 5,369,034, which is assigned to CEM Corporation of Matthews, N.C.

Although the simple application of microwave energy to devices in sealed vessels has some advantages, the technique becomes particularly useful when the reactions inside the vessels can be monitored while microwaves are being applied. Thus, in a typical microwave assisted chemistry system, a plurality of similar reactions are carried out at the same time in separate closed vessels that are placed together in a single cavity and then concurrently exposed to microwaves from a single source. Typically, one of the vessels carries temperature and pressure measuring devices. This "sensor vessel" is monitored and the conditions therein are assumed to be representative of the conditions in the remainder of the vessels to which microwaves are being applied.

Stated differently, in certain microwave assisted systems, a group of reaction vessels (typically six or eight) is placed into the microwave device at the same time, and often on a turntable that rotates as the microwaves are being applied. As noted above the wavelength of microwaves is typically larger than the items being heated, so that stationary items are not always evenly exposed to the microwaves. Accordingly, smaller items such as reaction vessels and relatively small amounts of chemical reagents are best moved on a periodic basis while being exposed to the microwaves. For similar reasons, consumer kitchen microwave ovens typically include fan-like stirrers to more evenly reflect microwaves within a cavity, or turntables for rotating food as it cooks. Alternatively, microwave cooking instructions typically tell the consumer to turn, stir, or otherwise move the food during the cooking process.

During microwave assisted chemistry, pressure is generally monitored for safety purposes; i.e. to make sure that the pressure generated by the chemical reaction remains within the pressure-containment limits of the device. A typical technique incorporates flexible tubing that runs from inside the vessel to an external pressure measuring device. Such an arrangement has been generally satisfactory for earlier generations of microwave assisted devices and vessels that operated at relatively lower pressure; e.g., about 200 pounds per square inch (psi). Vessels are now available, however, that can operate at internal pressures of 600, 900, or even 1500 psi. The typically available tubing materials cannot withstand such higher pressures and thus previous pressure measurement techniques cannot match the improvements in the vessels.

Additionally, measuring the gas pressure inside the vessel fails to take into account other stresses that can affect the vessel, particularly the stresses resulting from thermal expansion.

Pressure can be measured, of course, by placing a pressure-measuring device inside the reaction vessels along with the chemical reagents and then monitoring the reactions as they proceed. Although conceptually attractive, internal measurement is limited by the frequent presence of concentrated mineral acids such as hydrochloric (HCl), sulfuric ($H_2SO_4$) and phosphoric ($H_3PO_4$) that are often used in microwave assisted chemistry. Because of their aggressive chemical natures, these acids tend to attack almost all other materials and very few types of measuring devices (whether for pressure, temperature, or other parameters) can withstand such attack on a repeated basis.

OBJECT AND SUMMARY OF THE INVENTION

Therefore, the need exists for apparatus and techniques in which the internal pressure can be measured in a microwave assisted chemistry system, but without the disadvantages of complex arrangements or chemical attack on the measuring device.

The invention meets this object with a microwave vessel system for external and noninvasive pressure monitoring and control which comprises a sealable reaction vessel formed of a material that is transparent to microwave radiation. The vessel includes a portion that is movable under the pressure generated by a chemical reaction inside the vessel while maintaining the reaction sealed inside the vessel. An external sensor is adjacent to the movable portion of the vessel for detecting the motion of the movable portion as that portion responds to pressure inside of the vessel. The invention includes means for maintaining the sensor against the movable portion, while microwaves are applied to the vessel so that the movement of the movable portion under pressure is detected by the sensor.

In another aspect, the invention comprises a noninvasive method of measuring the pressure inside a reaction vessel during the application of microwave radiation to chemical reagents by applying microwave radiation to the chemical reagents inside the vessel and in which the vessel has a portion that moves externally in response to the generation of gas pressure inside. The method further comprises placing the movable portion of the vessel against the external sensor that generates a signal in response to movement against it, and then converting the sensing signal into a measure of pressure inside the vessel.

In another aspect, the invention comprises a system of microwave assisted chemistry that includes a source, a waveguide, a cavity, and a plurality of the reaction vessels in the cavity each of which has the external and noninvasive pressure measuring capabilities recited above.

The foregoing and other objects and advantages of the invention and the manner in which the same are accomplished will become clearer based on the following detailed description taken in conjunction with the accompanying drawings in which:

DETAILED DESCRIPTION

Figure 1:
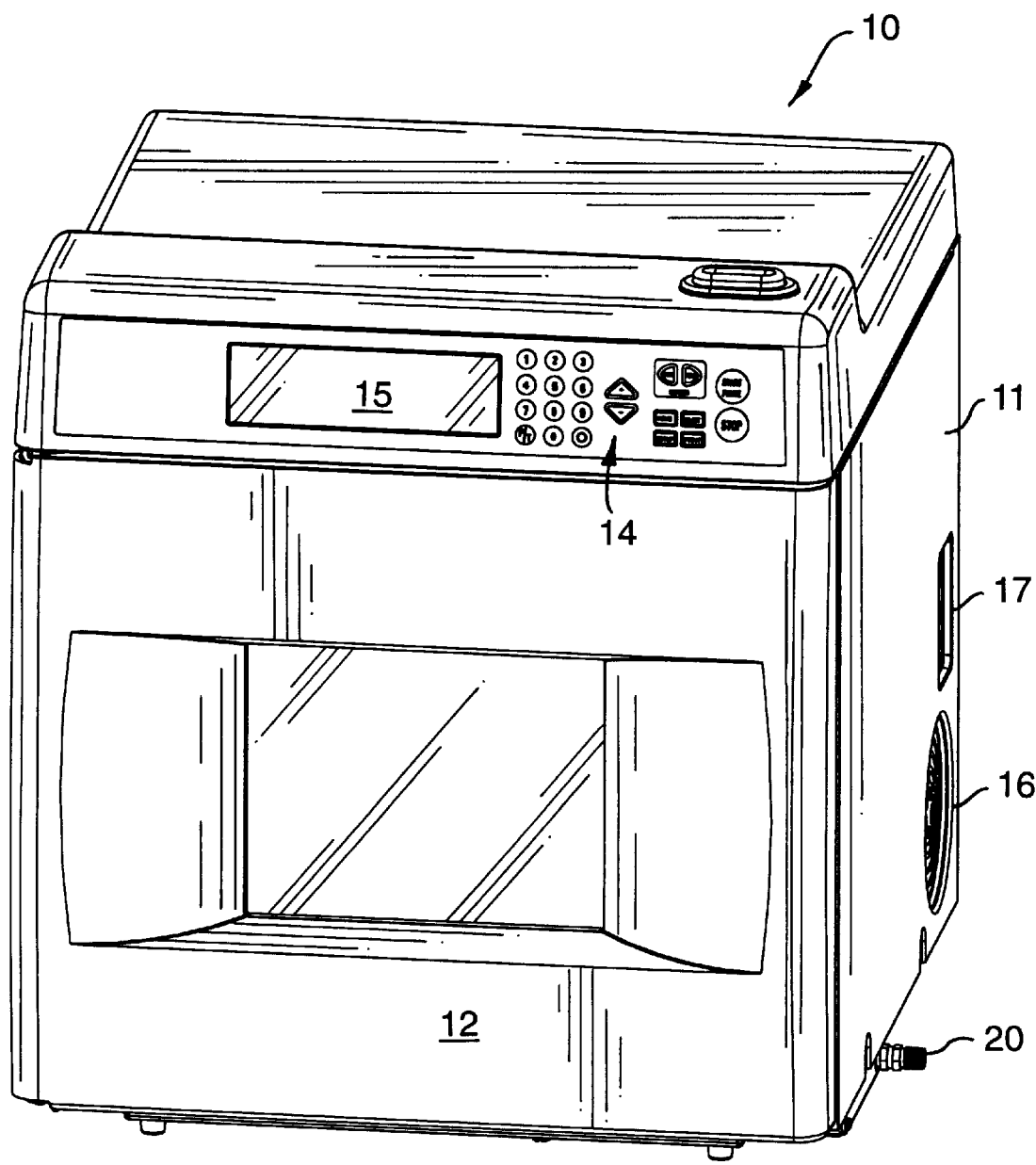
FIG. 1 is a perspective view of a laboratory device for microwave assisted chemistry.

The present invention is a microwave vessel system for external and noninvasive pressure monitoring and control. FIG. 1 illustrates a typical laboratory microwave device, broadly designated at 10. The basic structure and operation of microwave devices such as 10 has been well described in other patents, including for example U.S. Pat. Nos. 4,566,312; 4,681,996; Re34,373; 4,882,286; 5,066,843; 5,206,479. All of these are commonly assigned with the present application and discuss the fundamental structure and operation of microwave devices such as the illustrated device 10. Accordingly, the specific details and operation of such devices will not be otherwise discussed herein except as is necessary or helpful in describing the present invention. As set forth in these prior patents, however, the microwave device 10 typically includes a housing 11, a source (not shown) of microwave radiation in the housing, a waveguide (not shown) in the housing in microwave communication with the source, and a cavity (or "resonator") typically positioned behind the door 12 of the microwave device 10. The cavity in the housing 11 is in microwave communication with the waveguide and the source. As will be discussed further herein, in typical microwave assisted chemical processes, a plurality of reaction vessels are placed together in the cavity in the device 10 in order to take advantage of the device's capability of applying microwave radiation to the cavity and thus heating the contents.

As FIG. 1 further illustrates, the typical device 10 also includes a series of controls illustrated broadly 14 along with a display 15 which typically incorporates display elements such as a liquid crystal display (LCD) or a light omitting diode (LED) type of display. FIG. 1 also illustrates a fan opening 16 as well as various ports 17 and 20 for power, communications, or air and fluids.

Figure 2:
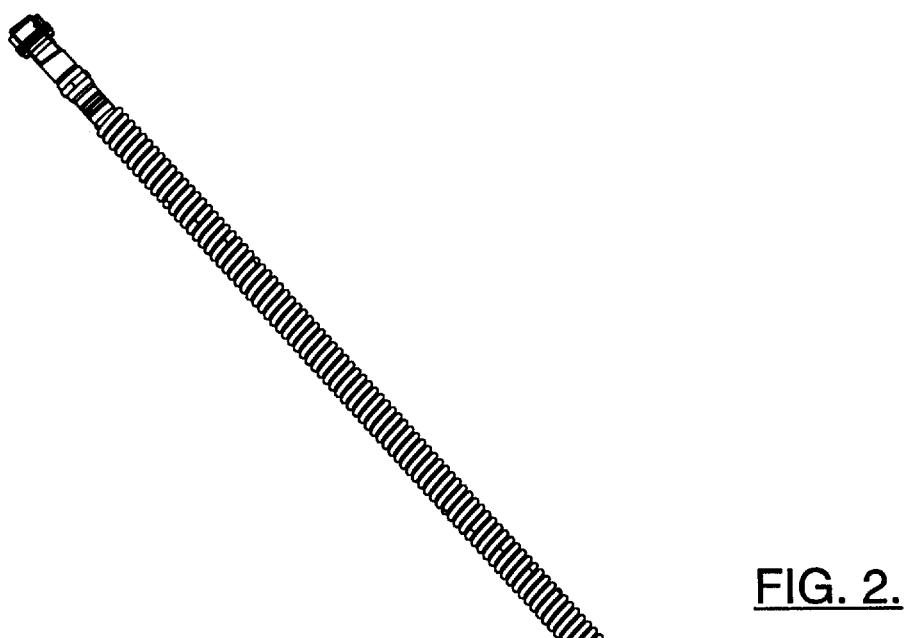
FIG. 2 is a perspective view of the vessel of the present invention.

FIG. 2 shows a microwave vessel system of the present invention for use in conjunction with the microwave device such as the device 10 illustrated in FIG. 1. The system includes a sealable reaction vessel 21 formed of a material that is transparent to microwave radiation. In preferred embodiments, the vessel 21 is formed of an engineering polymer such as polytetrafluoroethylene (PTFE) and is wrapped in a woven sheet of flat yarns formed from fiberglass fibers. Such devices are marketed under the designation UDV-10 by CEM Corporation of Matthews, N.C. the assignee of the present invention, and are described for example in commonly assigned U.S. Pat. No. 5,520,886.

Figures 5, 6:
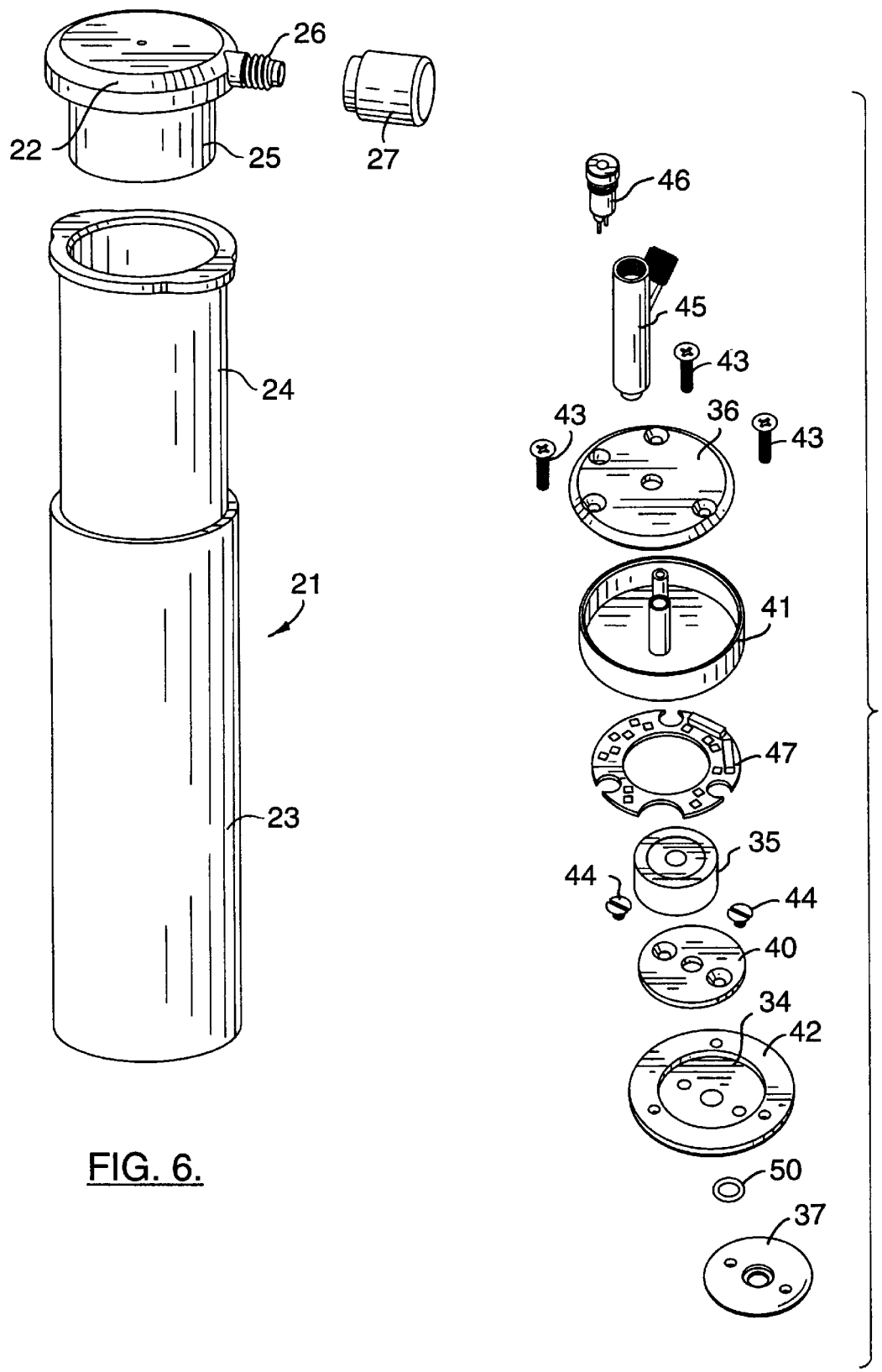
FIG. 5 is an exploded view of the pressure sensor in FIG. 4.
FIG. 6 is a partially exploded perspective view of the reaction vessel also illustrated in FIGS. 2 and 3.

The sealable reaction vessel 21 includes a portion illustrated in the drawings as the lid 22 that is movable under pressure, typically gas pressure, generated by a chemical reaction inside the vessel 21 while still maintaining the reaction sealed inside the vessel 21. In preferred embodiments, and as best illustrated in FIG. 6, the vessel 21 is formed of an outer sleeve 23 and an inner sleeve 24 and the lid 22 has a collar 25 depending therefrom that fits inside the inner sleeve 24. The combination forms a dynamic seal, meaning that under normally expected pressures, the pressure itself urges the lid to fit more tightly with the inner sleeve 24 thus increasing the seal's effectiveness. Under greater than expected pressures, however, the vessel and lid are sufficiently deformable to allow the high pressure gases to escape under a "soft" failure of the vessel rather than as the explosion of a more brittle vessel (as has been the case with previous pressure vessels). As FIG. 6 indicates, the lid 22 is movable under the gas pressure generated by a chemical reaction inside the vessel.

In preferred embodiments, the lid 22 also includes a pressure release valve formed from the threaded portion 26 and its cap 27 which holds a pressure release disc (not shown) inside the cap 27 and against a pressure relief opening in the threaded portion 26. Such pressure release valves are also well understood in this art and are illustrated for example, in commonly assigned U.S. Pat. No. 5,369,034.

Figure 3:
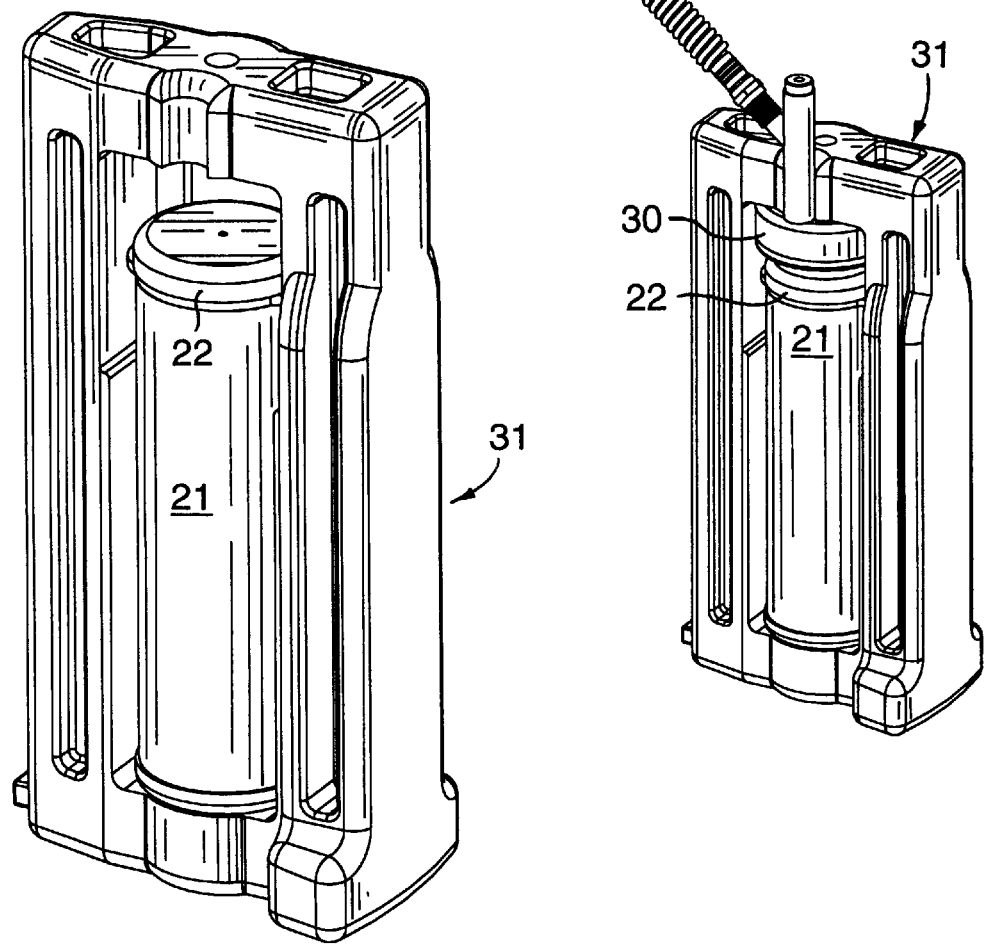
FIG. 3 is a view of the vessel and frame according to the present invention.

The vessel system further includes means, shown as the frame broadly designated at 31, for maintaining the sensor 30 against the movable portion (i.e., the lid 22) of the vessel 21 while microwaves are applied 21 so that the movement of the lid 22 under pressure is detected by the sensor. In preferred embodiments, the frame 31 is formed of a material, most preferably a polymer, that is transparent to microwave radiation and can be formed to be either flexible or rigid as may be desired or necessary under the operating conditions of any particular microwave system. As illustrated in FIGS. 2 and 3, the frame 31 is typically molded into a shape that is most convenient for its eventual end use, for example being mounted in a rack of a plurality of such vessels and sensors.

Figure 4:
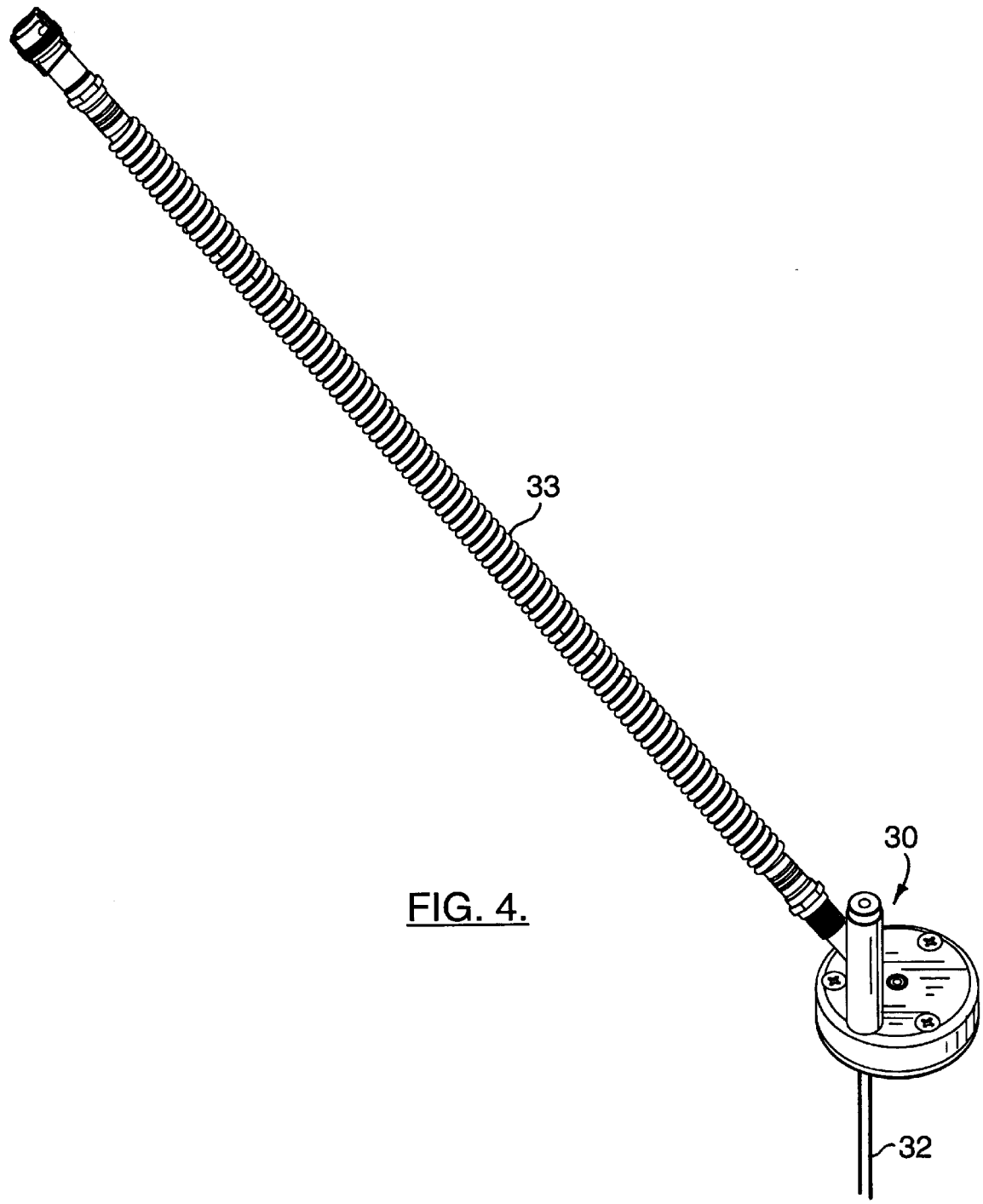
FIG. 4 is a perspective view of the pressure sensor portion of the invention.

FIGS. 2, 3, and 4 illustrate that the external sensor 30 can be simply slipped into place between the lid 22 of the vessel 21 and the frame 31. In preferred embodiments, the sensor 30 generates a signal, typically an electronic signal, and includes means for converting the signal into an indication of pressure within the vessel. The electronic components and related techniques for converting a signal generated by a sensor into a corresponding reading of a property such as temperature or pressure is well understood in the electronic arts and will not be otherwise explained in detail herein. Exemplary circuitry and the like is described for example in Dorf, THE ELECTRICAL ENGINEERING HANDBOOK (1994).

It will also be understood that under normally expected conditions, the movement of the movable portion of the vessel can be very small, e.g. on the order of thousandths of an inch.

It will be further understood that although the drawings illustrate the sensor 30 as being positioned above the lid 22, the invention is not limited to this orientation, and that other orientations—for example with the sensor 30 positioned beneath the vessel 21 but still between the vessel 21 and the frame 31—are within the scope of the invention and the claims.

In preferred embodiments, the external sensor comprises a housing that substantially avoids absorption of microwave radiation and in the most preferred embodiments comprises a metal (for shielding the electronic components inside) coated with a polymer (which helps provide environmental protection).

It will be understood by those familiar with electromagnetic radiation that with respect to particular wavelengths such as microwaves, some materials are transparent, other materials will absorb, other materials will reflect, and yet other materials are simply unaffected. Thus, as perhaps best illustrated in FIGS. 4 and 5 the external sensor 30 is preferably circular in shape rather than a polygon and incorporates rounded edges between its circumference and its top and bottom surfaces. The polymer coating is preferably polytetrafluoroethylene (PTFE). FIG. 4 shows that in preferred embodiments the sensor 30 also includes a temperature sensing device such as a thermocouple 32 and can be connected to other electronic circuitry through the flexible coaxial cable 33 and its associated quick-disconnect fittings.

Thus, in another aspect the invention comprises a sensor for externally measuring the pressure inside a sealed reaction vessel. In this aspect, the invention comprises a flexible surface illustrated as the stainless steel diaphragm 34 that moves in response to movement that bears against the diaphragm 34. The sensor further includes a strain gauge illustrated as the transducer 35 that generates a signal responsive to the movement of the stainless steel diaphragm 34, and a shield formed of the housing elements to be described herein, that prevents microwave radiation from substantially affecting the stainless steel diaphragm 34 or the transducer 35.

FIG. 5 also illustrates that the shield comprises a generally cylindrical metal housing that is formed by the assembly of an upper load washer 36, a load button 37, a lower load washer 40, and a center ring 41. FIG. 5 further illustrates that the stainless steel diaphragm 34 is supported by a lower ring 42 to which it is spot welded or soldered as may be desired or necessary. The assembly is held together by two sets of bolts 43 and 44 respectfully. FIG. 5 also illustrates that the external sensor can include the threaded tube 45 that provides access to and through the sensor to the interior of the vessel where desired or necessary for placement of a thermal couple or other device. A connector jack 46 can be incorporated as well to make the necessary electrical connections.

The strain gauge 35 is preferably a transducer such as an ENTRAN® Model ELF-1000 with a range of approximately 2,500 pounds (Entran Devices, Inc., 10 Washington Avenue, Fairfield, N.J. 07004). As noted, the transducer can be connected to electrical circuitry either within the sensor assembly such as the circuitry 47 illustrated in FIG. 5 or can be additionally connected to circuitry outside the sensor through the coaxial cable 33. An O-ring 50 can complete the assembly of the overall sensor 30. The ELF-1000 is a washer-shaped load cell with a high level output of 250 mV that can measure both steady state and dynamic compression loads and can be calibrated in either pounds or Newtons.

The stainless steel diaphragm 34 is maintained as the sole flexible item in the external. sensor with the remainder of the housing and sensor elements being rigid so that movement against the stainless steel diaphragm 34 is substantially entirely affected by the movement of the diaphragm 34 against the strain gauge 35. This arrangement helps insure that the movement of the vessel lid under pressure is accurately transmitted to the strain gauge 35. Stated progressively, the pressure exerted by the vessel is transferred to the diaphragm 34 and from the diaphragm to the strain gauge 35.

As another advantage, the sensor of the present invention measures the total stress that the application of heat and the generation of pressure exert against the vessel and its frame. Stated differently, the usual purpose of pressure measurement is to avoid approaching; the physical limits of the vessel, or of the vessel and its frame. The internal gas pressure, however, may not be identical to the total force experienced by the vessel and the frame. Because the invention measures the effect of forces between the vessel and the frame, including expansion forces exerted by the frame and vessel as they become warmer, the invention more accurately monitors and presents the desired information.

As further noted above, in many circumstances, a plurality of vessels, sensors, and frames according to the present invention are incorporated into a system that can be concurrently irradiated with microwave radiation in a device such as the device 10 illustrated in FIG. 1. In such circumstances, the ability to monitor pressure in each vessel is particularly useful and the device 10 will comprise means for moderating the microwave radiation from the microwave source (which typically is a magnetron but can also be other devices such as a klystron or a solid state source) in response to the pressure or temperature detected by any one or more of the pressure or temperature sensors incorporated in the system. Typically, the frames of the system are incorporated in a rack in the cavity upon which they can be rotated to be more evenly exposed to the microwave radiation.

Thus, in another aspect, the invention comprises the method of externally measuring the pressure inside a reaction vessel during the application of microwave radiation to chemical reagents inside the vessel. In this aspect, the invention comprises applying microwave radiation to chemical reagents inside a microwave transparent vessel in which the vessel of a portion that moves externally in response to the generation of gas pressure therein; placing the movable portion of the vessel against a sensor that generates a signal in response to movement against, and then converting the sensor signal into a measure of pressure inside the vessel.

In the drawings and specification, there have been disclosed typical embodiments of the invention, and, although specific terms have been employed, they have been used in a generic and descriptive sense only and not for purposes of limitation, the scope of the invention being set forth in the following claims.

That which is claimed is:

1. A microwave vessel system for pressure monitoring and control of individual reaction vessels, said system comprising:

at least one reaction vessel formed of a material that is transparent to microwave radiation;

said reaction vessel including a portion that is movable under pressure generated by a chemical reaction inside said vessel while maintaining the reaction sealed inside said vessel; and a sensor external to each vessel of said system and adjoining said movable portion of each vessel for detecting the motion of said movable portion as said portion responds to pressure generated inside each vessel;

means external to each vessel for maintaining said adjoining sensor against said movable portion while microwaves are applied to each vessel so that the movement of said movable portion under pressure is detected by said sensor, and means external to each vessel for converting the detection response of each sensor into an indication of pressure within each individual vessel.

2. A microwave reaction system according to claim 1 wherein said maintaining means comprises a frame that surrounds said reaction vessel and said sensor.

3. A microwave vessel system according to claim 1 wherein said movable portion comprises a lid for sealing said reaction vessel.

4. A microwave vessel system according to claim 2 wherein:

said frame comprises a material that is transparent to microwave radiation; and said sensor comprises a housing that substantially avoids absorption of microwave radiation.

5. A microwave vessel system according to claim 4 wherein said frame comprises a polymeric material and said sensor housing comprises a metal.

6. A microwave vessel system according to claim 4 wherein said frame is flexible.

7. A microwave vessel system according to claim 4 wherein said frame is rigid.

8. A microwave vessel system according to claim 2 and further comprising:

a source of microwave radiation;

a waveguide in communication with said source; and a cavity for positioning said vessel, frame and sensor therein.

9. A microwave vessel system according to claim 8 and comprising a plurality of said vessels, frames and sensors in said cavity.

10. A microwave vessel system according to claim 8 wherein said microwave source comprises a magnetron.

11. A microwave vessel system according to claim 8 wherein said microwave source comprises a solid state device.

12. A microwave vessel system according to claim 1 and further comprising a temperature sensor in said vessel.

13. A microwave vessel system for individual pressure monitoring and control of individual reaction vessels, said system comprising:

at least one cylindrical reaction vessel formed of a material that is transparent to microwave radiation;

a lid for closing each reaction vessel;

a collar depending from said lid;

said lid being movable under pressure generated by a chemical reaction inside each vessel while maintaining the reaction sealed inside each vessel;

a frame that surrounds each reaction vessel; and a sensor between said frame and adjoining said lid for detecting the motion of said lid as said lid moves in response to pressure generated inside each vessel, and means external to each vessel for converting the detection response of each sensor into an indication of pressure within each individual vessel.

14. A microwave vessel system according to claim 13 wherein said sensor comprises:

a flexible diaphragm for bearing against said lid; and a strain gauge responsive to said diaphragm for detecting the movement of said diaphragm generated by the movement of said lid.

15. A microwave vessel system according to claim 13 wherein said lid further comprises a controllable pressure release valve.

16. A microwave vessel system according to claim 13 wherein said cylindrical reaction vessel comprises an outer sleeve and an inner sleeve and wherein said collar depending from said lid fits inside said inner sleeve.

17. A microwave vessel system according to claim 14 wherein said frame comprises a polymeric material transparent to microwave radiation and said sensor housing comprises a metal coated with a polymer.

18. A microwave vessel system according to claim 13 wherein said frame is flexible.

19. A microwave vessel system according to claim 13 and further comprising a temperature sensor in said vessel.

20. A microwave vessel system according to claim 13 and further comprising:

a source of microwave radiation;

a waveguide in communication with said source; and a cavity for positioning said vessel, frame and sensor therein.

* * * * *